United States Patent [19]

Richmond

[11] 4,239,885
[45] Dec. 16, 1980

[54] PROCESS FOR THE PREPARATION OF DIACETONE ACRYLAMIDE

[75] Inventor: Henry Richmond, White House Station, N.J.

[73] Assignee: American Cyanamid Company, Stamford, Conn.

[21] Appl. No.: 920,040

[22] Filed: Jun. 28, 1978

Related U.S. Application Data

[63] Continuation-in-part of Ser. No. 859,623, Dec. 12, 1977, abandoned.

[51] Int. Cl.$^3$ .................. C07D 413/12; C07C 97/16
[52] U.S. Cl. .................. 544/97; 564/131; 564/204
[58] Field of Search .................. 260/561 N; 544/97

[56] References Cited

U.S. PATENT DOCUMENTS

| 3,277,056 | 10/1966 | Coleman | 260/561 N |
| 3,425,942 | 2/1969 | Coleman | 260/561 N |
| 3,542,875 | 11/1970 | Raymond | 260/561 N |
| 3,649,688 | 3/1972 | Gordon et al. | 260/561 N |

FOREIGN PATENT DOCUMENTS

| 897209 | 5/1962 | United Kingdom | 260/561 N |
| 1045869 | 10/1966 | United Kingdom | 260/561 N |

Primary Examiner—Winston A. Douglas
Assistant Examiner—Raymond K. Covington
Attorney, Agent, or Firm—Charles F. Costello, Jr.

[57] ABSTRACT

A process is disclosed whereby acrylonitrile and diacetone alcohol are reacted in at least 93% sulfuric acid to form a novel intermediate reaction product which is recovered as a crystalline solid, washed with an organic solvent to remove colored oily impurities along with sulfuric acid, and hydrolyzed to produce diacetone acrylamide, a reactive monomer useful for preparing polymeric components of photographic films and adhesives. The intermediate reaction product is identified as 5,6-dihydro-6-hydroxy-4,4,6-trimethyl-2-vinyl-1,3(4H)-oxazine sulfate (1:1).

1 Claim, 1 Drawing Figure

PROCESS FOR THE PREPARATION OF DIACETONE ACRYLAMIDE

This application is a continuation-in-part of Ser. No. 859,623 filed Dec. 12, 1977 now abandoned.

BACKGROUND OF THE INVENTION

This invention relates to a new process for the preparation of diacetone acrylamide (also referred to hereinafter as DIAC), also known as N-(1,1-dimethyl-3-oxobutyl)acrylamide, which is represented by formula (I).

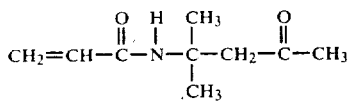

Applicant is not aware of any prior art reference which, in his judgment as one skilled in the art of preparing diacetone acrylamide, would anticipate or render obvious the process of the instant invention; however, for the purpose of fully developing the background of the invention and establishing the state of the requisite art, the following references are set forth.

In U.S. Pat. No. 3,649,688, an improved method is disclosed for preparing DIAC by reacting acrylonitrile with diacetone alcohol in the presence of sulfuric acid, the improvement comprising preparing a mixture of acrylonitrile and sulfuric acid, said sulfuric acid being at least 93% concentration, and the molar ratio of sulfuric acid to acrylonitrile being at least 1.6 to 1, introducing the diacetone alcohol into said mix at a temperature below 30° C. and maintaining said temperature during the reaction of the alcohol with the acrylonitrile, and recovering the DIAC from the reaction mixture. However, the product obtained is yellow-colored and contains about 5-10% by weight of acrylamide by-product.

In U.S. Pat. No. 3,542,867, an improved method is disclosed for preparing diacetone acrylamide by reacting diacetone alcohol, or mesityl oxide, or at least 2 moles of acetone in the presence of acrylonitrile and sulfuric acid, the improvement consisting of diluting the reaction mixture with water to a sulfuric acid content of 25-80% by weight, extracting the DIAC from the acidic reaction mixture with a water-immiscible organic solvent and recovering the DIAC from the extract.

In U.S. Pat. No. 3,542,875, an improved method is disclosed for preparing DIAC by reacting one mole of acrylonitrile with at least one mole of diacetone alcohol or mesityl oxide, or with at least two moles of acetone, in the presence of at least one mole of sulfuric acid, neutralizing the reaction mixture by addition of alkali to a pH at least above 7.5 and subsequently extracting with a water-immiscible organic solvent and recovering DIAC therefrom, the improvement consisting of heating the organic solution of DIAC at 50°-100° C. with aqueous alkali and recovering DIAC from the organic solution.

The DIAC produced by the process of the present invention has advantages over that produced by the processes of U.S. Pat. Nos. 3,542,867 and 3,542,875 in that it requires no further purification after isolation. The product obtained is substantially free of colored and polymeric by-products.

In U.S. Pat. No. 3,277,056, a series of equations is disclosed to illustrate the preparation of diacetone acrylamide by reacting diacetone alcohol and acrylonitrile in the presence of sulfuric acid. A hypothetical intermediate in this reaction is assigned formula (II)

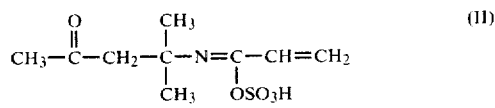

with the understanding that the formula is only illustrative. However, no intermediate such as (II) is actually isolated.

In general, the prior art teaches the preparation of DIAC by reacting acrylonitrile and 4-hydroxy-4-methyl-2-pentanone in the presence of at least 93% sulfuric acid, the mole ratios of said sulfuric acid and acrylonitrile to said 4-hydroxy-4-methyl-2-pentanone being about 1-2 and 1-1.5 moles, respectively, at a temperature below 15° C., allowing the reaction mixture to warm up to ambient to moderately elevated temperatures to complete the reaction, cooling the reaction mixture, contacting the reaction mixture with water and a water-immiscible organic solvent, neutralizing the aqueous phase with an alkalizing agent, separating the organic phase, stripping the organic phase of volatile materials, and recovering N-(1,1-dimethyl-3-oxobutyl)acrylamide therefrom.

DIAC is useful in photographic films, adhesives, as a reactive cross-linking monomer in unsaturated polyester resins, as a stabilizer in paper and glass reinforced prepregs, and as an additive in hydrocarbon oils. For a description of how to use as an oil additive, see for example, U.S. Pat. No. 3,227,056, Example 18, which is incorporated herein by reference.

In order to obtain DIAC of acceptable color and purity for use in photographic films, it has been generally necessary either to distill or recrystallize the crude product.

There is a need, therefore, for a process that will give high yields of essentially colorless DIAC, having a melting point above 54° C., which does not have to be purified by subsequent recrystallization or distillation.

SUMMARY OF THE INVENTION

In accordance with the present invention, there is provided a process for preparing N-(1,1-dimethyl-3-oxobutyl)acrylamide via a novel crystalline intermediate reaction product comprising reacting acrylonitrile and 4-hydroxy-4-methyl-2-pentanone in the presence of at least 93% sulfuric acid, at a temperature below about 20° C., to form a reaction mixture; heating the resulting reaction mixture up to a temperature of about 55° C. to complete the reaction; cooling the reaction mixture to about 15° C. and adding a suitable organic solvent thereto, while maintaining the temperature at about 15°-20° C., to precipitate a crystalline intermediate reaction product from said reaction mixture; washing said intermediate reaction product with a suitable organic solvent to remove oily impurities and sulfuric acid therefrom; dissolving the crystalline intermediate in water and contacting the resulting aqueous solution with a suitable water-immiscible organic solvent to form a liquid two-phase mixture consisting of an aqueous phase and an organic phase; neutralizing or alkalizing the aqueous phase with an alkalizing agent; separating the neutralized or alkalized aqueous phase; and recovering N-(1,1-dimethyl-3-oxobutyl)acrylamide from the organic phase.

In a preferred embodiment, after separating the neutralized or alkalized aqueous phase, the organic phase is stripped of volatile materials before recovering N-(1,1-dimethyl-3-oxobutyl)acrylamide therefrom.

In a more preferred embodiment, after separating the neutralized or alkalized aqueous phase, the organic phase is contacted with a decolorizing agent, preferably after stripping volatile materials from the organic phase, the decolorizing agent is separated, and the N-(1,1-dimethyl-3-oxobutyl)acrylamide is recovered from the organic phase.

In the preferred embodiments, the crystalline intermediate is precipitated from the reaction mixture by adding acetone thereto, and the water-immiscible organic solvent of the dissolving step is toluene. Still more preferably, the water-immiscible organic solvent of the dissolving step is a recycled mother liquor from the liquid organic phase of the recovering step. Preferably, the recycled mother liquor from the recovery step is toluene.

There is also provided a process for preparing the above-described crystalline intermediate, 5,6-dihydro-6-hydroxy-4,4,6-trimethyl-2-vinyl-1,3-(4H)-oxazine sulfate (1:1) a novel compound represented by formula (III),

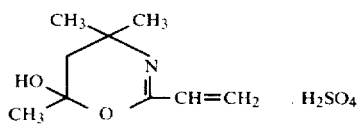

by reacting acrylonitrile and 4-hydroxy-4-methyl-2-pentanone in the presence of at least 93% sulfuric acid, at a temperature below about 20° C., to form a reaction mixture; heating the resulting reaction mixture up to a temperature of about 55° C. to complete the reaction; cooling the reaction mixture to about 15° C. and adding a suitable organic solvent thereto, while maintaining the temperature at about 15°-20° C. to precipitate 5,6-dihydro-6-hydroxy-4,4,6-trimethyl-2-vinyl-1,3-(4H)-oxazine sulfate (1:1), and recovering the same. In this process the suitable organic solvent is selected from the group consisting of acetone, methyl isobutyl ketone, mesityl oxide, and isopropanol.

FIG. 1 is an infrared absorption spectrum of the compound 5,6-dihydro-6-hydroxy-4,4,6-trimethyl-2-vinyl-1,3-(4H)-oxazine sulfate (1:1).

The processes of the present invention offer the following advantages. The DIAC obtained is essentially colorless, essentially free of polymeric materials and acrylamide, and melts above 54° C. The purity of the DIAC obtained is so high that recrystallization or distillation is unnecessary. This results in a substantial saving in operating costs. By recycling the toluene mother liquors, the yield of DIAC can be increased to as high as 45% of theoretical based on diacetone alcohol. Isolation of the crystalline intermediate of formula (III) renders the process operationally flexible since it can be stored and used at a later time.

DESCRIPTION OF THE PREFERRED EMBODIMENT

Figure 1:
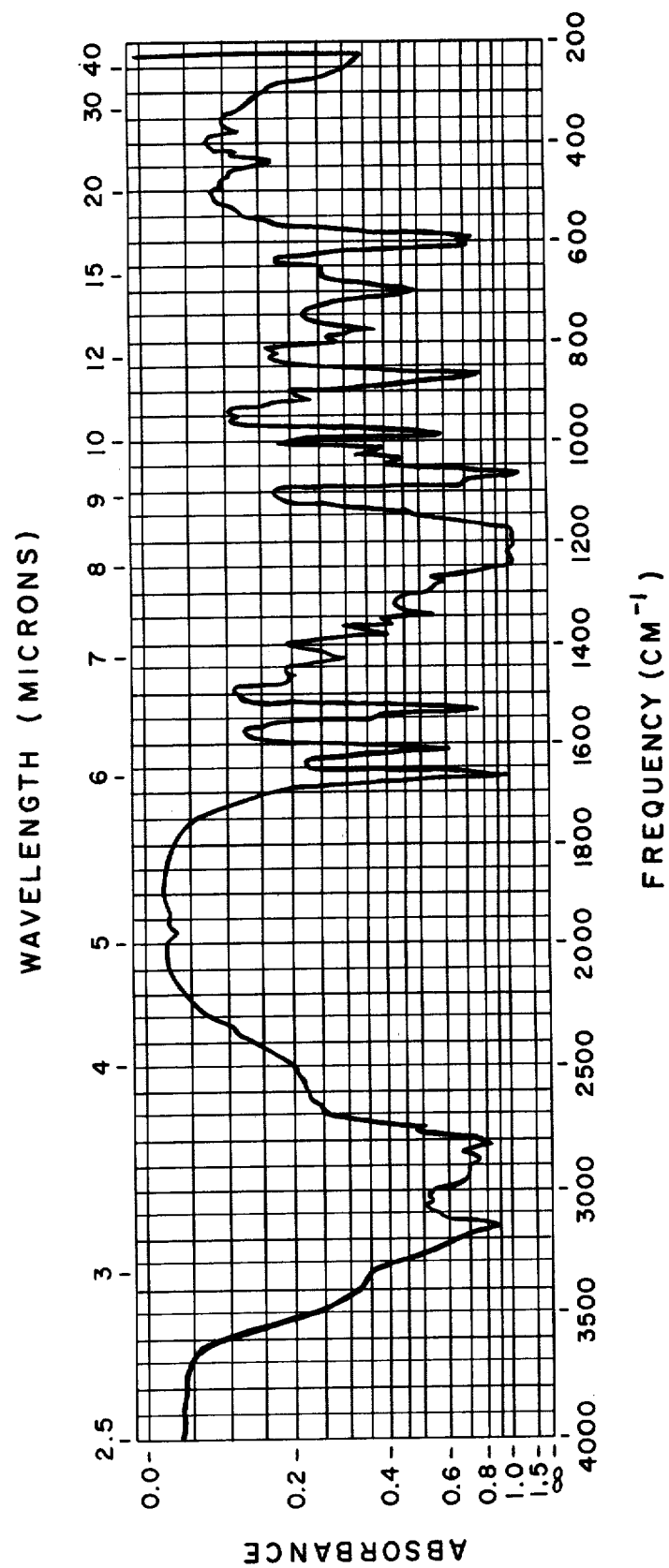

The process of this invention may be divided into the following stages:

(1) The formation and isolation of the crystalline intermediate reaction product, referred to hereinafter as the intermediate.
(2) The removal of impurities from the intermediate by washing with an appropriate solvent.
(3) The neutralizing or alkalizing of the intermediate to form DIAC.
(4) The removal of colored impurities from the DIAC by treatment of a solution of the DIAC with a decolorizing agent.
(5) The isolation of the DIAC.

The various stages of the present invention are described in detail below:

(1) FORMATION AND ISOLATION OF THE INTERMEDIATE

At least 93% sulfuric acid, preferably 96-98%, is cooled to about −10° C. to 20° C., preferably about 0°-5° C., and a mixture of acrylonitrile and diacetone alcohol is added thereto over a period of 1-20 hours, preferably 2-4 hours, while maintaining the temperature of the reaction mixture at −10° C. to 20° C., preferably about 0°-5° C. About 1-2 moles of sulfuric acid and about 1-1.5 moles of acrylonitrile are used per mole of 4-hydroxy-4-methyl-2-pentanone. In the most preferred embodiment, about 2 moles of sulfuric acid and about 1-1.2 moles of acrylonitrile are used per mole of 4-hydroxy-4-methyl-2-pentanone. The reaction mixture is stirred about 0-20 hours at −10° C. to 20° C., preferably ½-1 hours at 0°-5° C., allowed to warm up to 30°-60° C. over a period 1-20 hours, preferably to 45°-50° C. over a period of 3-6 hours, held at 30°-60° C. for a period of ½-20 hours, preferably at 45°-50° C. for a period of 1-3 hours, cooled to 10°-30° C., preferably to 10°-20° C., allowed to stand until the crystallization of the intermediate from the reaction mixture is complete, and the crystals are then recovered.

In an alternative preferred embodiment, the procedure of (1) is followed in every detail up to and including the cooling step after the warm up step. The reaction mixture is then diluted with a suitable organic liquid solvent to precipitate the intermediate from the solution. Suitable organic solvents include acetone, methyl isobutyl ketone, ethanol, isopropanol, 1-butanol, 2-butanol, 2-methyl-1-propanol, 2-methyl-2-propanol, methyl ethyl ketone, diethyl ketone, mesityl oxide, and the like. The resulting slurry is stirred at 0°-30° C., preferably at 15°-20° C., for a period of about ½-20 hours, preferably about 1-3 hours, and then processed following the procedures of (2) to (5) below.

(2) PURIFICATION OF THE INTERMEDIATE

The crude crystals from (1) are washed with a suitable organic liquid solvent to remove sulfuric acid, oily colored impurities and by-product acrylamide therefrom. Suitable solvents include acetone, ethanol, isopropanol, 1-butanol, 2-butanol, 2-methyl-1-propanol, 2-methyl-2-propanol, methyl ethyl ketone, methyl isobutyl ketone, diethyl ketone, mesityl oxide, and the like. The preferred solvent is acetone. If an alcohol is used to wash the crystals, it should be cold, about −10° C. to 0° C.

(3) NEUTRALIZATION OR ALKALIZATION OF THE INTERMEDIATE

The washed crystals from (2) are dissolved in water at ambient temperature using about 0.5 part to about 2 parts of water per part of intermediate and the resulting solution is mixed with a suitable water-immiscible organic solvent in which DIAC is soluble, using about 1–2 parts by volume of said water-immiscible organic solvent per part by weight of intermediate. Suitable water-immiscible organic solvents include naphtha, chloroform, methyl isobutyl ketone, dibutyl ether, aromatic hydrocarbons such as benzene, toluene, xylene, and the like. The preferred water-immiscible organic solvent is toluene.

The stirred two-phase mixture is cooled to about 5°–30° C., preferably about 15°–20° C., and an alkalizing agent, preferably 50% caustic soda, is added to adjust the pH of the aqueous layer to about 7–12, preferably about 9–10, to convert the intermediate to DIAC. It is critical that the washed crystals from (2) be dissolved in water and mixed with the water-immiscible organic solvent before adding the alkali in order to avoid the formation of low-molecular-weight polymers. On completion of the addition, the temperature should be between 32° C. and 40° C. Keeping the temperature above 32° C. avoids the precipitation of sodium sulfate, while keeping the temperature below 40° C. avoids the formation of polymers. The two-phase mixture is stirred for about ½–20 hours, preferably about ½–7 hours, to complete the extraction of the DIAC into the water-immiscible organic solvent, and the aqueous phase is separated after allowing the mixture to settle.

(4) THE REMOVAL OF COLORED IMPURITIES

The organic phase from (3) is dried to a water content of about 0.1–1% by weight, preferably about 0.1–0.5%, by azeotropic distillation under vacuum while keeping the temperature of the solution below 40° C. The dried solution is then stirred with finely powdered, heat-activated alumina, for example activated Alumina F-1 (Aluminum Company of America), using about 0.05–1 part, preferably 0.1–0.2 part of No. 325 mesh activated alumina per part by volume of dried organic, for a period of about ½ hour to remove colored impurities and the mixture is clarified by filtration. Other decolorizing agents which may be used include carbon black, Super-Filtrol ® (Filtrol Corporation) and the like. In a most preferred embodiment, the organic phase is stripped of volatile materials before being contacted with the decolorizing agent.

(5) THE ISOLATION OF DIAC

The clear filtrate from (4) is cooled to about −10° C. to 20° C., preferably about −8° C. to 10° C., and stirred thereat for about 1–20 hours, preferably about 2–8 hours, to crystallize the DIAC. The crude DIAC is then recovered by filtration, washed with a cold (−5° to −10° C.) water-immiscible organic solvent, preferably toluene at about −8° C., and dried. The overall yield of 4-hydroxy-4-methyl-2-pentanone is about 30–35% of theoretical, depending on the quality of the product desired. Reuse of the recovered mother liquor in (3) increases the overall yield to about 40–45% of theoretical. The product obtained melts above 54° C. and contains less than 0.1% by weight of acrylamide.

The following examples further illustrate the invention. All parts and percentages are by weight unless otherwise specified. All ranges expressed are inclusive of both numbers.

EXAMPLE 1

Preparation of
5,6-Dihydro-6-Hydroxy-4,4,6-Trimethyl-2-Vinyl-1,3-(4H)-Oxazine Sulfate (1:1)

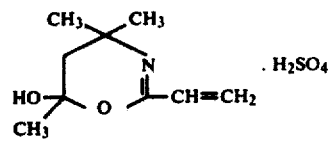

Sulfuric acid (392 grams; 98% real; 3.92 moles) is cooled to 0° C. and a mixture of acrylonitrile (113.5 grams; 2.14 moles) and diacetone alcohol (203.5 grams; 1.75 moles) is added thereto over 1.5 hours while maintaining the temperature at 0°–5° C. The resulting mixture is stirred at 0°–5° C. for 0.5 hour, allowed to warm up slowly to 40°–42° C., held thereat for 3 hours and then cooled at 15° C. Acetone (443 grams; 0.625 ml./gram of reaction mixture) is added to the reaction mixture while keeping the temperature at 15°–20° C. Upon completion of the addition, the solution is cooled to 0°–5° C. and held thereat for 4 hours. The resulting crystals are separated by filtration, washed with acetone and dried to obtain 234 grams of product which has the infrared absorption spectrum shown in FIG. 1. The yield of product is 50% of theoretical based on diacetone alcohol.

Calculated for $C_9H_{17}NO_6S$: C,40.45%; H,6.41%; N,5.24%; S,11.97%; Found: C,39.77%; H,6.35%; N,5.10%; S,11.74%; $H_2O$, 1.55%

Corrected for 1.55% $H_2O$: C,40.40%; H,6.28%; N,5.18%; S,11.92%

Calculated for % $H_2SO_4$: 36.7%

EXAMPLE 2

Sulfuric acid (392 grams; 98% real; 3.92 moles) is cooled to 0° C. and a mixture of acrylonitrile (113.5 grams; 2.14 moles) and diacetone alcohol (203.5 grams; 1.75 moles) is added thereto over 1.5 hours while maintaining the temperature at 0°–5° C. The resulting mixture is stirred at 0°–5° C. for 0.5 hour, allowed to warm up slowly to 40°–42° C., held thereat for 3 hours and then cooled at 15° C.

Acetone (500 mls.) is added to the reaction mixture while maintaining the temperature between 15°–20° C. After stirring for 1 hour, the resulting crystals are filtered, washed with acetone and dried. The crystals (283 grams) are dissolved in water (500 mls.) and toluene (500 mls.) is added thereto to form a two-phase mixture. The mixture is cooled to 15° C., and caustic soda (110 mls. of 50% real) is added thereto while maintaining the temperature between 15°–20° C. After stirring for 0.5 hour, the aqueous layer is separated and the organic layer is dried by azeotropic distillation (176 mls. of distillate). The residual solution is stirred with heat-activated alumina (10 grams; 325 mesh) for 0.5 hour and filtered. The filtrate is cooled to 10° C. and the resulting crystals are recovered and dried to obtain 93 grams of diacetone acrylamide (31% of theoretical; m.p. 55.8°–56.7° C.).

In the manner described above, substituting ethanol, isopropanol, methyl ethyl ketone, mesityl oxide or methyl isobutyl ketone for the acetone, similar crystals are obtained.

EXAMPLE 3

Sulfuric acid (98%; 391.6 grams; 3.91 moles) is charged to a suitable reactor vessel and cooled to 0° C. A mixture of acrylonitrile (113.5 grams; 2.14 moles) and diacetone alcohol (203.5 grams; 1.75 moles) is added thereto over a period of 1.5 hours while maintaining the reaction mixture at 0°-5° C. The reaction mixture is then stirred at 0°-5° C. for an additional 0.5 hour and allowed to slowly warm up to 25° C. The reaction mixture is then carefully and slowly heated to 40°-42° C., held thereat for 3 hours, and then cooled to 10° C. After standing at 10°-20° C. for 96 hours, the resulting crystals are recovered by filtration.

The crystals are dissolved in water (500 mls.), toluene (500 mls.) is added thereto, the two-phase mixture is cooled to 15° C. and aqueous sodium hydroxide (50% real; 110 mls.) is added thereto while keeping the temperature at 15°-20° C. After stirring for about 0.5 hour, the aqueous layer is separated and the toluene layer is dried by azeotroping off the water. The residual toluene solution is stirred with activated alumina (10 grams of No. 325 mesh) for 0.5 hour and clarified by filtration. The filtrate is then cooled to 10° C., and the resulting crystals are recovered by filtration and dried to obtain diacetone acylamide (50 grams; 20% of theoretical) which melts at 55.0°-57.2° C.

EXAMPLE 4

The procedure of Example 2 is followed in every detail utilizing 500 mls. of toluene mother liquors from a previous preparation of DIAC to extract the alkalized product from the aqueous phase. The yield of DIAC is 39% of theoretical. The product is of acceptable purity.

EXAMPLE 5

The procedure of Example 2 is followed in every detail utilizing the toluene mother liquors recovered from Example 4 to extract the hydrolysis product from the aqueous phase. The yield of DIAC is 45% of theoretical. The product is of acceptable purity.

I claim:
1. The compound of the formula:

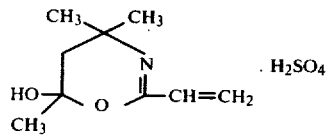

* * * * *